United States Patent [19]
Hovland et al.

[11] Patent Number: 5,733,457
[45] Date of Patent: Mar. 31, 1998

[54] TECHNIQUE FOR DISINFECTING EXTRACORPOREAL FLUID TREATMENT SYSTEMS

[75] Inventors: Roy S. Hovland, Denver; Byron W. Larson, Arvada; Jo-Ann B. Maltais, Morrison, all of Colo.

[73] Assignee: COBE Labortories, Inc., Lakewood, Colo.

[21] Appl. No.: 760,480

[22] Filed: Dec. 5, 1996

Related U.S. Application Data

[62] Division of Ser. No. 477,491, Jun. 7, 1995, Pat. No. 5,647,984.

[51] Int. Cl.$^6$ .................. A61L 2/00; A61M 1/14; B01D 61/30
[52] U.S. Cl. .................. 210/636; 210/194; 210/195.1; 210/195.2; 210/321.69; 422/1
[58] Field of Search .................. 210/194, 195.1, 210/195.2, 636; 422/1, 38, 14; 210/321.69

[56] References Cited

U.S. PATENT DOCUMENTS

| | | | |
|---|---|---|---|
| 3,441,136 | 4/1969 | Serfass et al. | 210/321.69 |
| 3,738,392 | 6/1973 | Cappelen et al. | |
| 4,018,684 | 4/1977 | Uffer | 210/140 |
| 4,122,010 | 10/1978 | Riede et al. | 210/90 |
| 4,331,540 | 5/1982 | Witsoe | 210/321.69 |
| 4,399,030 | 8/1983 | Hlavinka et al. | 210/321.69 |
| 4,728,496 | 3/1988 | Petersen et al. | 422/1 |
| 4,774,415 | 9/1988 | Biegel et al. | |
| 5,032,265 | 7/1991 | Jha et al. | 210/321.68 |

FOREIGN PATENT DOCUMENTS

| | | |
|---|---|---|
| 61-244372 | 4/1985 | Japan. |
| 1579 177 | 11/1980 | United Kingdom. |
| WO 96/09080 | 3/1996 | WIPO. |

*Primary Examiner*—John Kim
*Attorney, Agent, or Firm*—Carol W. Burton, Esq.; Holland & Hart, LLP

[57] ABSTRACT

An extracorporeal fluid treatment apparatus which is selectively operable in a disinfecting mode or a treatment mode includes an inlet line, a pre-treatment portion, an input pump, a heater, an input shunt, a filtration device, a post-treatment portion, a drain line and an output shunt. The apparatus also includes a combination of valves which are selectively positionable in disinfecting mode to create an input fluid circuit which includes the pre-treatment portion and the input shunt, and which is in fluid isolation from the post-treatment portion and from the filtration device. In disinfecting mode, the valves are also selectively positionable to create an output fluid circuit which includes the post-treatment portion and the output shunt, and which is in fluid isolation from the pre-treatment portion and from the filtration device. In disinfecting mode, a heated input fluid is circulated in the input fluid circuit and a heated output fluid is circulated in the output fluid circuit until disinfection of each of the input and output fluid circuits is achieved. The apparatus optionally includes a heat exchanger through which heat is transferred while in disinfecting mode from the input fluid in the pre-treatment portion to the output fluid in the post-treatment portion.

4 Claims, 4 Drawing Sheets

TECHNIQUE FOR DISINFECTING EXTRACORPOREAL FLUID TREATMENT SYSTEMS

This application is a division of application Ser. No. 08/477,491 filed Jun. 7, 1995, issued U.S. Pat. No. 5,647,984.

FIELD OF THE INVENTION

This invention relates to disinfection of extracorporeal fluid treatment systems, and more particularly, to new and improved apparatus and methodology for disinfecting fluid lines of an extracorporeal blood treatment apparatus.

BACKGROUND OF THE INVENTION

Extracorporeal fluid treatment typically involves the removal of a body fluid from a patient, treatment of the fluid externally to the patient, and return of the treated fluid to the patient. Blood is one body fluid for which conventional extracorporeal techniques have been developed. Using these techniques, blood is treated to extract materials from the blood and/or add materials to augment the blood prior to return of the treated blood to the patient. More particularly, extracorporeal blood treatment may be accomplished by removing the blood from the patient in a continuous flow and introducing the blood into a chamber containing a filtration unit, wherein the blood is conducted past a semi-permeable membrane. The semi-permeable membrane selectively allows material in the blood to pass through the membrane for removal from the blood and/or allows material to pass through the semi-permeable membrane to the blood, to or from a fluid separately flowing past the semi-permeable membrane of the filtration unit. After passage of materials to and from the blood, the treated blood is discharged from the filtration device for return to the patient. The material which has been removed from the blood is separately discharged from the filtration unit.

One exemplary extracorporeal blood treatment is hemodialysis. In conventional hemodialysis treatment, treated water is provided to a hemodialysis machine and mixed therein with a predetermined amount of one or more solutes or concentrates to form a dialysate. The water is heated in the hemodialysis machine before and/or after addition of solutes and/or concentrates, typically to a body temperature of approximately 37° C. This fresh dialysate is then conducted into a filtration device or dialyzer of the hemodialysis machine. Once in the dialyzer, the dialysate flows past a side of a semi-permeable membrane, typically in a counter-current direction to that of the blood from a patient flowing in the dialyzer on an opposite side of the membrane. Waste matter, typically organic molecular ions, plasma and water, is transferred from the blood to the dialysate due to osmotic, diffusive and convective action. Further, in a process known as ultrafiltration, excess fluid may be removed from the blood by establishing a pressure differential across the membrane that pulls the excess fluid from the blood across the membrane and combines it with the dialysate in the dialyzer. Dialysate discharged from the filtration device, sometimes referred to as spent dialysate, may be conducted past a heat exchanger where heat from the spent dialysate is transferred to the treated water being provided to the hemodialysis machine on the "fresh" side. Thereafter, the spent dialysate is conducted to a drain line for collection, analysis and/or, more typically, discharge.

A single hemodialysis machine generally does not run continuously, but rather is used to treat blood in discrete treatment sessions, usually with different patients. The equipment may be idle between treatments and may accumulate deposits in the flowpath. Further, spent dialysate may contain molecules or material which can accumulate in the flowpath after the dialyzer, which can provide a nutrient source for bacterial growth and accumulation therein. The use of such equipment for different patients, the need to prevent patient pyrogenic reactions due to bacterial endotoxin, and the possible accumulation of dirt or other unsterile substances in the equipment make periodic cleaning and disinfection of the equipment desirable.

Cleaning is typically achieved by rinsing the affected portions of the flowpath with bleach solution. Chemical and/or heat disinfection are methods commonly used to disinfect the non-disposable portions of hemodialysis equipment.

Chemical disinfection techniques include the conduction of chemicals such as formaldehyde, bleach, peracetic acid or other disinfectant solutions through the non-disposable portions of such equipment. There can be, however, significant cost associated with the purchase and use of such chemicals. In addition, chemical disinfection techniques require a technician to specially add, remove and/or dispose of the chemical disinfectant, while disconnecting the hemofiltration device and other components from the dialysate equipment. Performance of these steps can take time away from the technician's other duties. With certain disinfectants, the technician who is cleaning the system must take special care when dealing with concentrated chemical solutions. Moreover, in disinfecting with chemicals, care must be taken to completely flush the chemicals, which may exhibit some degree of toxicity, from the portion of the flowpath in which the dialysate is prepared and through which fresh dialysate flows during treatment, to avoid any possibility of delivering the chemical to the patient through the membrane of the dialyzer. There may also be environmental concerns or regulations which restrict the discharge of the disinfecting chemicals to public waste disposal facilities. Container disposal can also be problematical.

Heat disinfection of extracorporeal blood treatment systems is well known. Heat disinfection of the fluid pathway of extracorporeal blood treatment systems is performed by circulating a fluid such as water, sterile water, or a disinfection solution throughout all such pathways of the equipment for a sufficiently long period of time, typically 15 minutes or more, at a sufficiently high temperature, typically from 80° C. to as high as 125° C. One way in which such disinfection is achieved is by conducting the solution (1) through the pathway which ordinarily receives treated water, (2) into the portions of the flowpath in which fresh dialysate is prepared with heated water and in which fresh dialysate flows during treatment, (3) bypassing the dialyzer, (4) into the portions of the flowpath in which spent dialysate flows during treatment, and (5) through the drain line to exit the machine. This technique is referred to herein as a single path once-through heat disinfection method.

Single path once-through heat disinfection discharges the heated fluid through the drain line to the drain. As a result, fluid continuously added to the system must be heated to temperature, which consumes additional power and results in additional cost.

This problem has been ameliorated in some hemodialysis systems by routing all or a portion of the heated fluid from the part of the flowpath in which spent dialysate flows during treatment back, to the part which receives treated water, or to the dialysate preparation portion, thereby conserving heat and reducing the power required to maintain adequate disinfection temperature. These techniques are referred to herein as single path heat disinfection methods with recirculation.

Although single path heat disinfection with recirculation reduces the power consumed by the disinfection process, it creates a new problem. The heated fluid, in passing through the spent dialysate line, may pick up material in the line deposited by spent dialysate during prior treatments. Such material may be subsequently carried into the dialysate preparation line and fresh dialysate lines. This creates a possibility of contamination which may potentially be passed on to patients subsequently treated with the equipment.

All single path heat disinfection methods may exhibit substantial heat loss between a point in the dialysate preparation line where the solution is heated and the drain line where solution is discharged from the system. This heat loss results in decreasing temperature from the dialysate preparation portion of the flowpath to the drain line which may result in incomplete disinfection of the flowpath approaching the drain line. The disinfection fluid in the dialysate preparation portion is sometimes heated to a temperature substantially above 90° C., for example at or around 125° C., so that the resulting fluid temperature gradient from the fluid in the dialysate preparation portion to the fluid in the drain line results in a low temperature of closer to 90° C. However, this technique can result in damage to equipment which may not be designed for repeated operation at such elevated temperatures or can require the incorporation of material capable of withstanding elevated temperatures, thereby increasing system cost.

It is against this background that the significant improvements and advancements of the present invention have taken place in the field of disinfecting extracorporeal treatment apparatus.

SUMMARY OF THE INVENTION

A significant object of the present invention relates to disinfection of an extracorporeal fluid treatment apparatus in a manner which minimizes the probability of transferring contaminants in the apparatus to patients subsequently treated with the apparatus.

Another object of the present invention relates to increased heating efficiency and lower power consumption when disinfecting the flowpath of an extracorporeal fluid treatment apparatus.

A further object of the present invention is the disinfection of the flowpath of extracorporeal fluid treatment apparatus without necessarily requiring use of chemical disinfectants.

A still further object of the present invention is the accomplishment of the aforementioned objects without allowing fluid that has contacted the fluid pathway downstream of a dialyzer to contact the fluid pathway upstream of the dialyzer in order to decrease the risk of infecting patients with residual material from patients previously treated with the apparatus.

In accordance with these and other objects, the present invention relates to a method for disinfecting the flowpath of an extracorporeal fluid treatment apparatus in which a fluid is heated and circulated in a pre-treatment portion of the apparatus and diverted away from the extracorporeal filtration device or dialyzer of the apparatus. In addition, a heated fluid is circulated in the post-treatment portion of the apparatus in isolation from the fluid in the pre-treatment portion and from the filtration device. Further, in accordance with these and other objects, the method also allows for heating the fluid in the post-treatment portion by heat transfer from the heated fluid flowing in the pre-treatment portion to the post-treatment portion fluid. Circulation of the fluids is maintained in each of the pre-treatment and post-treatment portions until disinfection of each of the pre-treatment and post-treatment portions is achieved.

Also in accordance with aforementioned objects, the extracorporeal fluid treatment apparatus which is ordinarily used to treat extracorporeal fluids from a patient is selectively operable in a disinfecting mode. The apparatus includes an extracorporeal filtration device or dialyzer having a chamber in which treatment of a patient's bodily fluids is conducted. The apparatus includes an inlet line through which a fluid is received and a pre-treatment portion in fluid communication with the inlet line in which the fluid is heated and may be further modified by addition of other materials. An input pump induces a flow of the fluid through the pre-treatment portion. When the apparatus is in treatment mode, the fluid in the pre-treatment line is conducted into the extracorporeal filtration device and thence into a post-treatment portion, where it is conducted by an output pump to a drain line.

When the apparatus is in disinfecting mode, an input shunt, which is in fluid communication with the pre-treatment portion, receives and diverts an input fluid flowing in the pre-treatment portion away from the filtration device and returns the fluid to the beginning of the pre-treatment portion. An output shunt is operatively positioned in the post-treatment portion for receiving and diverting an output fluid flowing therein back into the beginning of the post-treatment portion.

The extracorporeal fluid treatment apparatus of the present invention optionally includes a heat exchanger through which the input fluid in the pre-treatment portion and the output fluid in the post-treatment portion pass without fluid communication with each other on opposite sides of the heat exchanger. When the apparatus is in treatment mode, heat is transferred from the output fluid in the post-treatment portion to the input fluid in the pre-treatment portion. When the apparatus is in disinfecting mode, heat may be transferred from the input fluid in the pre-treatment portion to the output fluid in the post-treatment portion.

The extracorporeal fluid treatment apparatus and method of the present invention permit the disinfecting of such an apparatus in a manner which minimizes the probability of contamination of the pre-treatment portion of the apparatus during disinfection by preventing post-treatment fluid from contacting pre-treatment fluid pathways. The possibility of contamination of patients subsequently treated with the apparatus is also thereby decreased. In addition, the disinfection technique of the present invention may be accomplished with minimized heat loss, thereby increasing the efficient use of power when disinfecting the apparatus. Further, disinfection of an extracorporeal fluid treatment apparatus using the techniques of the present invention may be accomplished without requiring the use of chemical disinfectants such as formaldehyde.

Further, in accordance with certain of the aforementioned objects, the fluids in the pre-treatment portion and post-treatment portion may be a chemical disinfectant, whereby an increased disinfection effect, or shortened disinfection time period, is achieved over that achievable with either heat and/or chemical disinfection in a single path once-through approach.

These and other features of the present invention can be better understood from the following detailed description of a preferred embodiment of the present invention taken in conjunction with the accompanying drawings that are described below.

DETAILED DESCRIPTION

Figure 1:
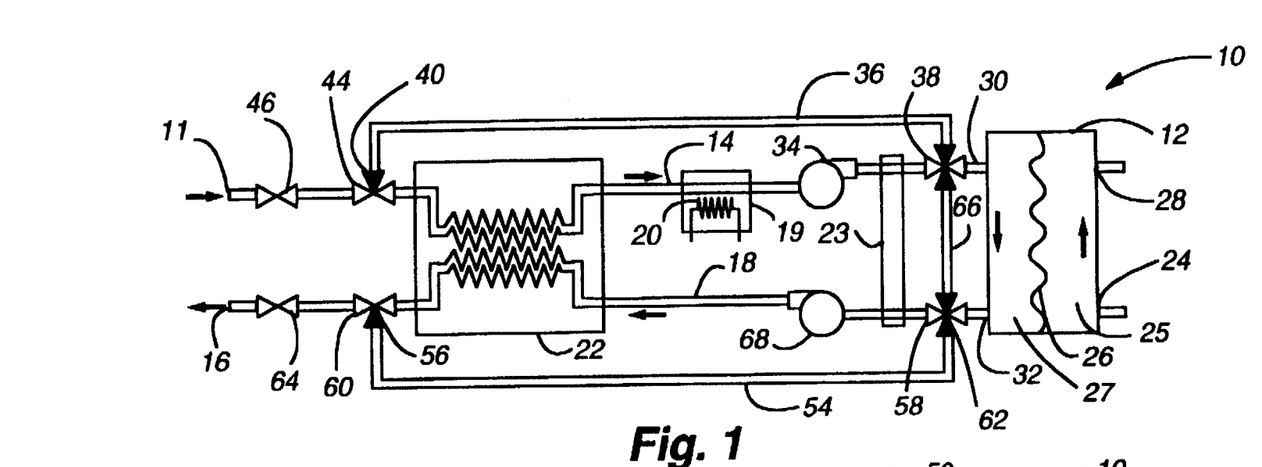
FIG. 1 is a functional schematic illustration of an extracorporeal blood treatment apparatus incorporating an embodiment of the present invention, illustrating flow of fluids in the apparatus when the apparatus is in a treatment mode.
Figure 2:
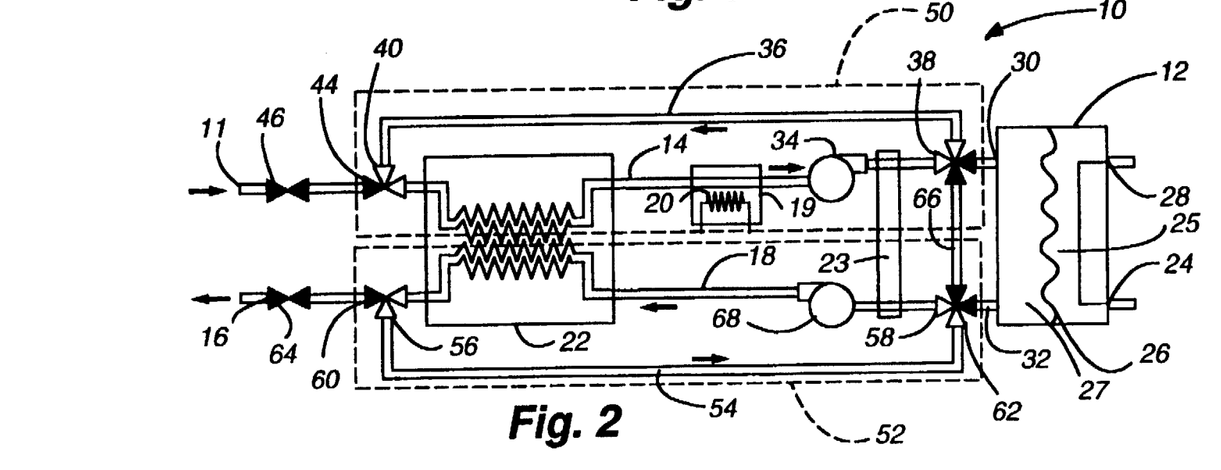
FIG. 2 is a functional schematic illustration of the extracorporeal blood treatment apparatus of FIG. 1, illustrating the flow of fluids in the apparatus when the apparatus is in a disinfecting mode.

A presently preferred embodiment of an apparatus 10 for extracorporeal treatment of blood from a patient (not shown) which may be disinfected according to the method of the present invention, is illustrated in FIGS. 1 and 2. The apparatus 10 includes an inlet line 11, an extracorporeal filtration device or dialyzer 12, a pre-treatment portion 14 operatively connected to the inlet line 11 and to the dialyzer 12, a drain line 16, and a post-treatment portion 18 operatively connected to the extracorporeal filtration device 12 and to the drain line 16. The apparatus 10 also preferably includes a dialysate preparation portion 19, including a heater 20, a heat exchanger 22, and an ultrafiltration portion 23.

The disinfection method of the present invention initially involves the isolation of the pre-treatment portion 14 and the post-treatment portion 18 from the extracorporeal filtration device 12. The pre-treatment portion 14 and post-treatment portion 18 are then both filled with a disinfection fluid, typically treated water from the inlet line 11. The pre-treatment portion 14 is then isolated from the post-treatment portion 18. A circulating flow of fluid is then maintained in the pre-treatment portion 14 and a circulating flow of fluid is maintained in the post-treatment portion 18. The fluids in each of the pre-treatment and post-treatment portions or sections 14 and 18 are heated to and maintained at or above 90° C. in order to disinfect each of the pre-treatment and post-treatment portions 14 and 18 of the apparatus 10. In the preferred embodiment, the temperature of the fluid flowing in the pre-treatment portion 14 is raised to approximately 95° C., or as hot as possible without boiling, and the fluid flowing in the post-treatment portion 18 is heated to disinfection temperature by heat transfer through the heat exchanger 22 from the fluid flowing in the pre-treatment portion 14. With regard to the fluids flowing in the apparatus 10 during the disinfecting process of the present invention, the fluid flowing in the pre-treatment portion 14 may be, but need not be, the same as the fluid flowing in the post-treatment portion 18 and either may or may not contain a chemical disinfectant or descaling agent.

More particularly, and with reference to FIG. 1, the extracorporeal blood treatment apparatus 10 of the present invention includes the dialyzer 12 having a blood input port 24, a blood chamber 25 separated by a semi-permeable membrane 26 from a dialysate chamber 27, and a blood output port 28. During treatment of blood from a patient, blood is continuously received from the patient through the blood input port 24 into the blood chamber 25 and is conducted out the blood output port 28 for return to the patient. While passing through the blood chamber 25, material in the blood is typically transferred across the membrane 26 of the dialyzer 12 from the blood to a dialysate solution flowing in the dialysate chamber 27 of the dialyzer 12 through a dialysate input port 30 and out a dialysate output port 32.

A number of components of the apparatus 10 are positioned upstream from the dialysate input port 30 of the dialyzer 12. Furthest upstream from the dialyzer 12 is the inlet line 11. The inlet line 11 is in selective fluid communication with the downstream pre-treatment portion 14. Fluid received in the inlet line 11 is conducted into and along the pre-treatment portion 14 by means of an input pump 34. Upon entering the pre-treatment portion 14 the fluid in the pre-treatment portion 14 is conducted through the heat exchanger 22 and dialysate preparation portion 19, past the heater 20 and through the ultrafiltration portion 23. The pre-treatment portion 14 is in selective fluid communication with the dialysate input port 30 of the dialyzer 12.

The post-treatment portion 18 is in selective fluid communication with the dialysate output port 32 of the dialyzer 12. The post-treatment portion 18 is also in selective fluid communication with the drain line 16, through which fluid flowing in the post-treatment portion 18 is discharged from the apparatus 10. Upon exiting the dialysate output port 32, the dialysate, now spent dialysate, is conducted through the ultrafiltration portion 23 and through the heat exchanger 22 to the drain line 16.

Referring now to FIG. 2 it can be seen that the apparatus 10 also includes an input shunt 36 which is selectively connected to the pre-treatment portion 14 at an input collection point 38 of the pre-treatment portion 14 adjacent a position on the pre-treatment portion 14 close to the dialysate input port 30 of the filtration device 12. The input shunt 36 also selectively opens into the pre-treatment portion 14 at an input return point 40 of the pre-treatment portion 14 which is upstream of the input collection point 38.

Fluid communication between the input shunt 36 and the pre-treatment portion 14 is selectively maintained by a first bypass valve 42 positioned in the pre-treatment portion 14 adjacent the input collection point 38, a second bypass valve 44 positioned in the pre-treatment portion 14 adjacent the input return point 40, and an inlet shutoff valve 46 positioned in the pre-treatment portion 14 adjacent the inlet line 11. When the first and second bypass valves 42 and 44 are selectively positioned as so described, the pre-treatment portion 14 and input shunt 36 together comprise an inlet fluid circuit 50 of the extracorporeal fluid treatment apparatus 10.

In an analogous manner, an output fluid circuit 52 includes the post-treatment portion 18 and an output shunt 54 which branches from the post-treatment portion 18 at an output collection point 56 adjacent the drain line 16. The output shunt 54 returns to the post-treatment portion 18 at an output return point 58 in the post-treatment portion 18 near the dialysate output port 32 of the filtration device 12. A third bypass valve 60 is operably positioned in the post-treatment portion 18 adjacent the output collection point 56. A fourth bypass valve 62 is operatively positioned in the post-treatment portion 18 adjacent the output return point 58 to divert fluid flowing in the output shunt 54 away from the dialyzer 12 and into the post-treatment portion 18. An output shutoff valve 64 is positioned in the drain line 16 to partially or completely block fluid flowing in the post-treatment portion 18 from entering the drain line.

It should be understood that FIGS. 1 and 2 are schematic diagrams only, and are intended to illustrate the present invention at a symbolic level. Thus, for example, while the component positioning is illustrative to show relative position (i.e. upstream or downstream), it should be understood that length of lines is symbolic only, for example the length of the pre-treatment portion 14 is not necessarily the same as the length of the input shunt 36. Indeed, in actual practice the input shunt 36 may be minimal in length, for example, if the input collection point 38 is near the input return point 40 within the apparatus 10. It is possible, for example, for the functionality of the input shunt 36 to be an element of the first bypass valve 42.

Moreover, other components of a conventional apparatus 10 may be positioned upstream from the dialysate input port 30 and downstream of the dialysate output port 32 which are not illustrated herein for sake of clarity. For example, an apparatus 10 may include one or more pressure sensors (not shown) to measure pressure at one or more locations in the pre-treatment portion 14. The dialysate preparation portion 19 of the apparatus 10 may also include one or more reservoirs (not shown) and lines (not shown) for supplying dialysate solutions and/or solutes to the pre-treatment portion 14. The apparatus 10 may also include means for mixing dialysate (not shown) and means for analyzing dialysate (not shown) so as to supply the desired amount and composition of dialysate to the dialyzer 12. Control of these and other components of the pre-treatment portion 14 and detection of alarm conditions are typically automatically accomplished by one or more preprogrammed computers (not shown), which receive and transmit signals to and from each of the components of the pre-treatment portion 14 across electrical circuitry (not shown).

The extracorporeal treatment apparatus 10 is preferably selectively operable in a treatment mode or a disinfecting mode. When the apparatus 10 is set to treatment mode (FIG. 1), the inlet shutoff valve 46 is set to an open position allowing treated water or other suitable fluid to be conducted through the inlet line 11 into the pre-treatment portion 14. The second bypass valve 44 is positioned to prevent the treated water or other fluid flowing in the pre-treatment portion 14 from entering the input shunt 36, and also to prevent any fluid present in the input shunt 36 from entering the pre-treatment portion 14. The first bypass valve 42 is positioned so as to prevent fresh dialysate flowing in the pre-treatment portion 14 from entering the input shunt 36 and directs the fresh dialysate flowing in the pre-treatment portion 14 towards the dialysate input port 30.

Also while in treatment mode, the third bypass valve 60 is positioned to direct spent dialysate or other fluid flowing in the post-treatment portion 18 into the drain line 16 and prevent such fluid from entering the output shunt 54. The fourth bypass valve 62 is positioned to prevent spent dialysate or other fluid flowing in the post-treatment portion 18 from entering the output shunt 54 at the output return point 58.

In disinfecting mode (FIG. 2), the first bypass valve 42 is positioned to direct the flow of treated water or other fluid flowing through the pre-treatment portion 14 into the input shunt 36 and away from the dialyzer 12. The second bypass valve 44 is positioned so as to direct the fluid flowing in the input shunt 36 into the pre-treatment portion 14 at the input return point 40. The inlet shutoff valve 46 is closed so as to prevent additional water or other fluid from entering the pre-treatment portion 14 from the inlet line 11 and also to prevent input fluid in the pre-treatment portion 14 from flowing back into the inlet line 11.

Also while in disinfecting mode, the third bypass valve 60 is positioned so as to divert output fluid flowing in the post-treatment portion 18 into the output shunt 54. The fourth bypass valve 62 is set so as to return output fluid flowing in the output shunt 54 to the post-treatment portion 18 and also to prevent the output fluid from flowing into the dialyzer 12. The output shutoff valve 64 is positioned so as to prevent some or substantially all of the output fluid flowing in the post-treatment portion 18 from discharge into the drain line 16.

Preferably, the first bypass valve 42 is also selectively positionable so as to direct an input fluid or other sterile fluid provided to and flowing in the pre-treatment portion 14 into a filtration device bypass line 66. The fourth bypass valve 62 is further preferably positionable to selectively divert the sterile fluid flowing in the bypass line 66 into the post-treatment portion 18. In this way, the sterile fluid introduced into the inlet line 11 or otherwise into the pre-treatment portion 14 can be conducted into the post-treatment portion 18 and then into output shunt 54 without contacting the dialyzer 12. The bypass line 66 may thus be used to fill the post-treatment portion 18 and the output shunt 54 with one or more fluids, for example, treated water, input fluid, disinfecting solution and cleansing solution, provided to the pre-treatment portion 14.

To disinfect the extracorporeal fluid treatment apparatus 10, an input fluid, for example, treated water, is introduced into the inlet line 11 and thence conducted into the pre-treatment portion 14. The first bypass valve 42 is positioned so as to direct the input fluid into the bypass line 66. The fourth bypass valve 62 is positioned to allow input fluid in the bypass line 66 to enter the post-treatment portion 18 and flow there along. The fluid is referred to herein as the output fluid, it being understood that the term "output fluid" is intended to encompass any fluid flowing in the output fluid circuit 52 without regard to how the fluid was provided thereto. The third bypass valve 60 is positioned to divert substantially all of the flow of output fluid in the post-treatment portion 18 into the output shunt 54 until it reaches the output return point 58, at which time the fourth bypass valve 62 is positioned to prevent additional input fluid from entering the post-treatment portion 16 from the bypass line 66 and cause the output fluid in the output shunt 54 to flow into the post-treatment portion 18 at the output return point 58. Once the input fluid flowing in the bypass line 66 is thus prevented from entering the post-treatment portion 18, the first bypass valve 42 is positioned to divert the input fluid flowing in the pre-treatment portion 14 into the input shunt 36. The second bypass valve 44 is positioned to cause the input fluid flowing in the input shunt 36 to return to the pre-treatment portion 14 at the input return point 40

Thereafter, the inlet shutoff valve 46 is closed to prevent additional fluid from entering the pre-treatment portion 14 from the inlet line 11 and also prevent input fluid in the pre-treatment portion 14 from flowing into the inlet line 11.

The input pump 34 in the pre-treatment portion 14 is operated continuously during the filling procedure just described, at first to conduct input fluid from the pre-treatment portion 14 into the bypass line 66, then into the post-treatment portion 18, and thereafter to circulate input fluid in the pre-treatment portion 14 through the input shunt 36 and back into the pre-treatment portion 14. An output pump 68 is also continuously operated while the filling procedure is conducted to assist in the filling of the output fluid circuit 52. While in the preferred embodiment the output pump 68 is operatively positioned in the post-treatment portion 18, it may also be located in the output shunt 54.

Although in the preferred embodiment input fluid is supplied to the pre-treatment portion 14 through the inlet line 11 and is supplied to the post-treatment portion 18 through the bypass line 66, other apparatus configurations and methodology may be implemented to supply solutions to the input and output fluid circuits 50 and 52 for disinfection thereof. For example, input fluid supplied through the inlet line 11 may be supplemented in all or part by solutions or solutes introduced directly into the pre-treatment portion 14 through lines or reservoirs attached thereto (not shown). Also by way of example, input fluid may be supplied directly to the pre-treatment portion 14 through a line (not shown) other than the inlet line 11. Furthermore, output fluid may be provided to the post-treatment portion through the drain line 16 (not shown), rather than through the inlet line 11, and provisions (not shown) may be made to supplement the output fluid with solutions or solutes introduced directly into the post-treatment portion 18 or output shunt 54 in a manner similar to that illustrated in U.S. Pat. No. 5,409,612, incorporated herein in its entirety by reference, or by a line connected to a pump or other uptake device which may be included in output shunt 54.

To disinfect the input fluid circuit 50 and the output fluid circuit 52 of the extracorporeal blood treatment apparatus 10, the input fluid in the pre-treatment portion 14 is heated by the heater 20 as the fluid passes thereby. Heat is then transferred via heat exchange from the input fluid in the input fluid circuit 50 to the output fluid flowing in the output fluid circuit 52 while the two fluids pass through the heat exchanger 22. Preferably the input fluid flowing in the input fluid circuit 50 is heated with the heater 20 until it reaches a temperature of approximately 95° C. Thereafter, the heater 20 is operated so as to maintain the temperature of the input fluid in the input fluid circuit 50 at somewhat above 90° C., in a manner which compensates for the heat transfer from the input fluid flowing in the input fluid circuit 50 to the output fluid flowing in the output fluid circuit 52 which takes place in the heat exchanger 22 and other heat losses. Circulation of fluid in the input fluid circuit 50 and in the output fluid circuit 52 is continued by operation of the input pump 34 and the output pump 68 until the temperature of the output fluid flowing in the output fluid circuit 52 has been maintained at or above 85° C. for a predetermined period of time required to disinfect the output fluid circuit 52, preferably approximately 10 to 15 minutes.

After disinfection of the input and output fluid circuits 50 and 52 has been achieved, the output shutoff valve 64 is opened to allow output fluid in the post-treatment portion 18 to drain into the drain line 16, the fourth bypass valve 62 is positioned to divert output fluid flowing in the post-treatment portion 18 into the drain line 16, the third bypass valve 60 is positioned to close access from the post-treatment portion 18 into the output shunt 54, the first bypass valve 42 is positioned to divert input fluid flowing in the pre-treatment portion 14 into the bypass line 66 and thence into the post-treatment portion 18, and the second bypass valve 44 is positioned to close the input shunt 36. Thereafter, the dialyzer 12 may be connected to the pre-treatment and post-treatment portions 14 and 18 and the apparatus 10 used for extracorporeal fluid treatment of a patient.

Alternatively, circulation of an input fluid in the input fluid circuit 50 and an output fluid in the output fluid circuit 52 may be conducted for a sufficiently long period of time at a sufficiently high temperature to disinfect the input and output fluid circuits 50 and 52, after which the input and output fluids are drained as described above and disinfection is followed by introduction of a cleansing solution to each of the input and output fluid circuits 50 and 52. The input and output fluid circuits 50 and 52 are then isolated, circulation of the cleansing solutions in each of the input and output fluid circuits 50 and 52 is separately maintained, and the cleansing solutions are drained from the input and output fluid circuits 50 and 52 as described above.

Although in the preferred embodiment described above, four bypass valves and two shutoff valves are disclosed, it should be understood that the functionality of the valves as required to practice the present invention, may be accomplished by a lesser or greater number of separate valves. For example, in the preferred embodiment the first bypass valve 42 is selectively positionable in three orientations which functions to divert input fluid exclusively to one of the dialysate input port 30, the input shunt 36 or the bypass line 66. However, this same functionality may be achieved by three separate valves (not shown), which, in predetermined combined alignments, direct input fluid in a desired direction. Also by way of example, if a bypass line 66 is not present in a particular apparatus 10 and an output fluid provided to the post-treatment portion 18 by means other than a bypass line 66, the functionality of the input bypass valve 32 as it relates to bypass line 66 may not necessarily be implemented.

Figure 3:
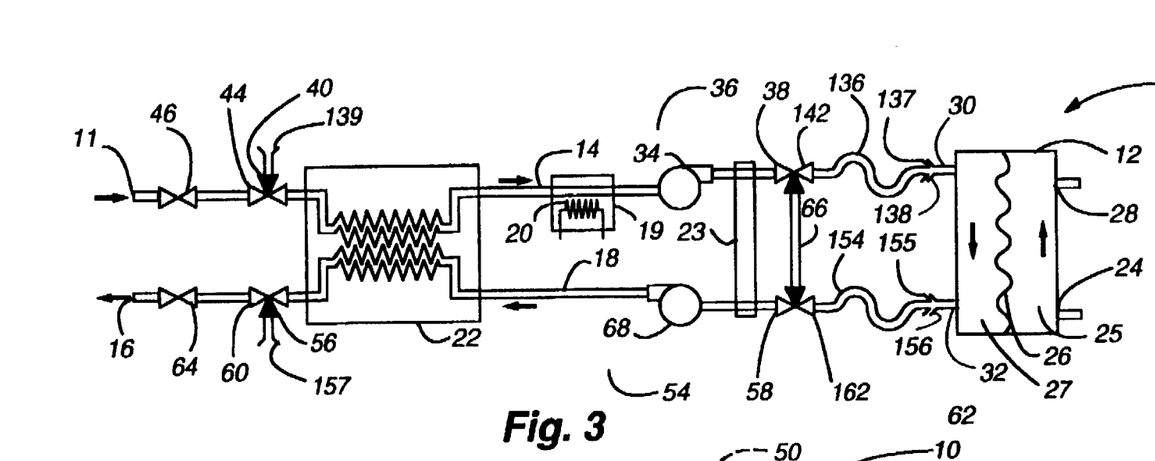
FIG. 3 is a functional schematic illustration of an extracorporeal blood treatment apparatus incorporating an alternative embodiment of the present invention, illustrating the flow of fluids in the apparatus when the apparatus is in the treatment mode.
Figure 4:
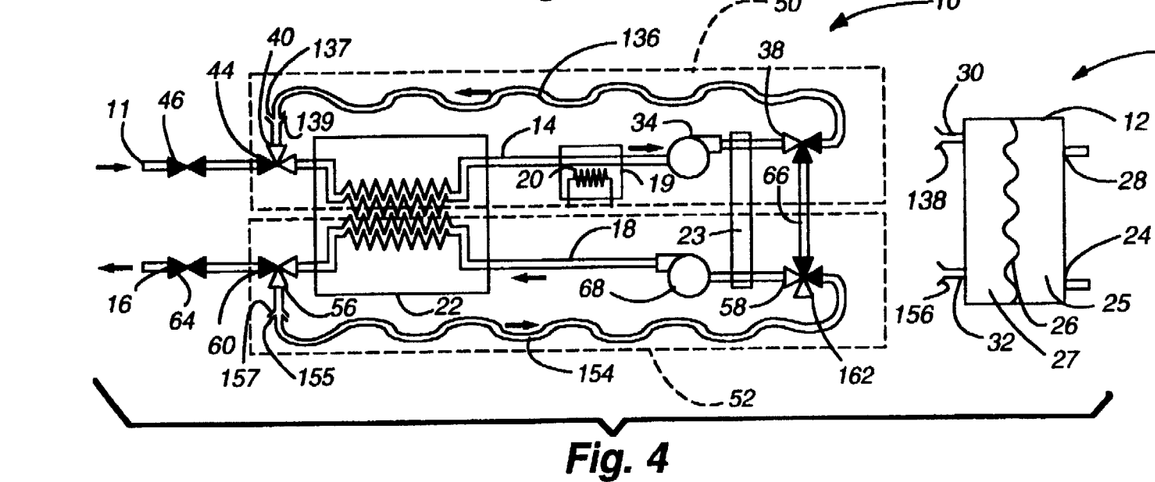
FIG. 4 is a functional schematic illustration of the extracorporeal blood treatment apparatus of FIG. 3, illustrating the flow of fluids in the apparatus when the apparatus is in a disinfecting mode.

FIGS. 3 and 4 illustrate an alternative preferred embodiment of the present invention. Reference numerals in FIGS. 3 and 4 denote the same elements as like numerals in FIGS. 1 and 2. Referring now to FIG. 3, in the alternative preferred embodiment during treatment, the dialysate input port 30 of the dialyzer 12 is operatively connected to the pre-treatment portion 14 by an input flexible hose 136 which mates at the dialyzer 12 by means of a conventional quick release female connector 137 on the hose 136 and a male connector 138 on the input port 30. During treatment, the dialysate output port 32 of the dialyzer 12 is operatively connected to the post-treatment portion 18 by an output flexible hose 154 which mates at the dialyzer 12 by means of an output quick release female connector 155 on the hose 154 and male connector 156 on the output port 32. An input loop male connector 139 is provided at the input return point 40 and an output loop male connector 157 is provided at the output collection point 56.

Referring now to FIG. 4, to initiate a disinfection procedure in accordance with the alternative preferred embodiment, the input hose female connector 137 is disconnected from the dialyzer 12 input port male connector 138 and connected to the input loop male connector 139, thus forming the input fluid circuit 50. The output hose female connector 155 is disconnected from the dialyzer output port male connector 156 and connected to the output loop connector 157, thus forming the output fluid circuit 52. Disinfection then proceeds as described above.

Figure 5:
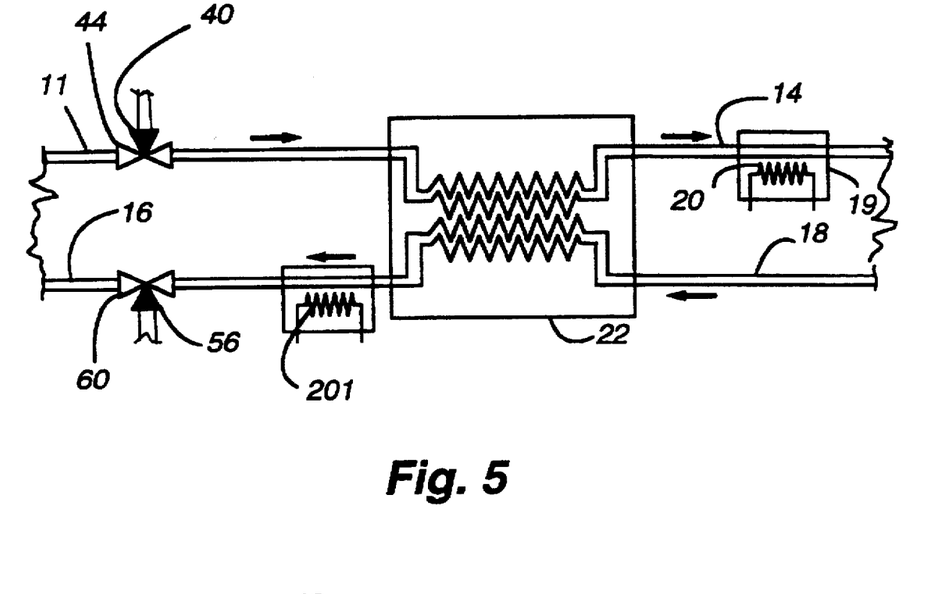
FIG. 5 is a partial functional schematic illustration of a variation of the extracorporeal blood treatment apparatus of FIGS. 1 and 2 or FIGS. 3 and 4.
Figure 6:
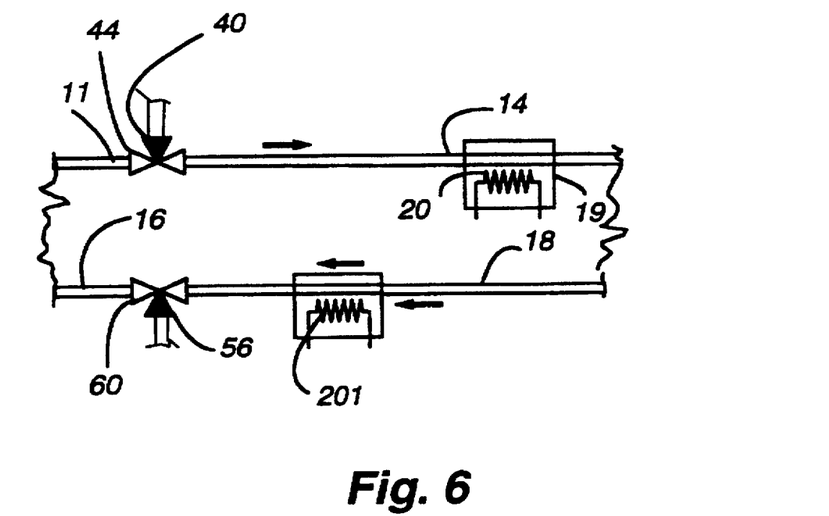
FIG. 6 is a partial functional schematic illustration of a further variation of the extracorporeal blood treatment apparatus of FIGS. 1 and 2 or FIGS. 3 and 4.

FIGS. 5 and 6 illustrate variations of the present invention in which an auxiliary heater 201 is provided to heat the fluid in the post-treatment portion 18. In the variation illustrated in FIG. 5, the auxiliary heater 201 supplements the disinfection heat provided to the output fluid circuit 52 (FIGS. 2 and 4) by the input fluid circuit 50 (FIGS. 2 and 4) by the heat exchanger 22 to shorten the disinfection time or increase its effectiveness.

In the variation illustrated in FIG. 6, there is no heat exchanger 22. The heater 20 provides the heat necessary for treatment and for disinfection of the input fluid circuit 50. The output loop heater 201 provides the heat necessary for disinfection of the output fluid circuit 52.

Figure 7:
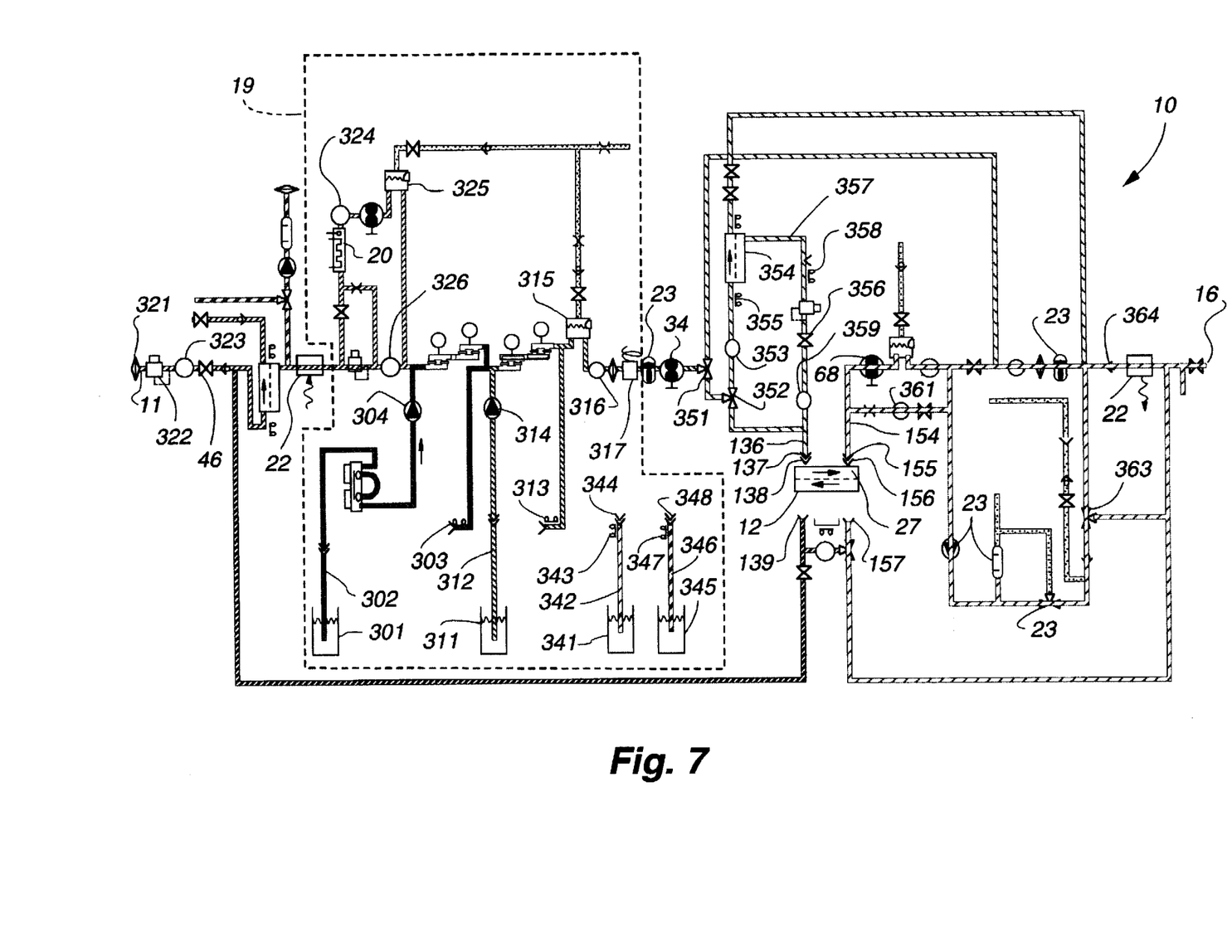
FIG. 7 is a functional schematic illustration of extracorporeal blood treatment apparatus incorporating a further alternative embodiment of the present invention.

Another embodiment of the present invention is illustrated in FIG. 7, with reference numerals of FIG. 7 denoting the same elements as like numerals in FIGS. 1 and 2. The apparatus 10 of FIG. 7 includes a bicarbonate reservoir 301, a bicarbonate conduit 302, a bicarbonate port switch 303 and a bicarbonate pump 304 for selectively supplying bicarbonate solution to the dialysate preparation portion 19 when the apparatus 10 is in treatment mode. The apparatus 10 includes an acid reservoir 311, an acid conduit 312, an acid port switch 313 and an acid pump 314 for selectively supplying a conventional, commercially available acidic solution to dialysate preparation portion 19. The apparatus 10 also includes a bubble trap 315, a temperature sensor 316, and a pH sensor 317. Positioned in the inlet line 11 upstream of the valve 46 inlet shutoff valve are an inlet filter 321, an inlet pressure regulator 322 and a inlet pressure switch 323. A control temperature sensor 324 is positioned downstream of the heater 20 and a degassing bubble trap 325 is positioned downstream of the sensor 324. A heater protection flow switch 325 allows for selectively bypassing the heater 20.

A cleaning solution reservoir 341, cleaning conduit 342, cleaning port switch 343 and cleaning connector 344 selectively supply cleaning solution to portions of the apparatus 10. A disinfectant reservoir 345, disinfectant conduit 346, disinfectant port switch 347 and disinfectant connector 348 selectively supply disinfectant to portions of the apparatus 10.

The apparatus 10 as shown in FIG. 7 also includes bypass valves 351 and 352, an ultrafilter pressure sensor 353, a clean dialysate ultrafilter 354, an ultrafilter bypass switch 355, isolation valve 356, infusate port 357, infusate port switch 358, pre-dialyzer pressure sensor 359, post-dialyzer pressure sensor 361, heat exchanger valve 363, and outlet check valve 364.

When the apparatus 10 illustrated in FIG. 7 is operated in disinfecting mode (not shown), the input loop male connector 139 is connected to the quick release female connector 137 on the hose 136, and the output loop male connector 157 is connected to the output quick release female connector 155 on the hose 154, thereby establishing the isolated input and output fluid circuits 50 and 52, respectively (not shown), discussed above in connection with FIGS. 1 and 2 and FIGS. 3 and 4.

In any case, construction of an apparatus 10 in accordance with the present invention, allows for heat disinfection of the apparatus 10 in such a way as to isolate the fluid flowing in the pre-treatment portion 14 from the fluid flowing in the post-treatment portion 18, thereby minimizing the risk of contamination of the pre-treatment portion 14 of the apparatus 10 during disinfection, but allowing both pre- and post-treatment portions 14 and 18 of the extracorporeal treatment apparatus to be disinfected either simultaneously or independently without cross-contamination of the pre-treatment portion by the post-treatment side. As a consequence, risk of contamination of patients subsequently treated with the apparatus 10 is also thereby decreased. When a heat exchanger 22 is installed in the apparatus 10, the disinfection technique of the present invention may be accomplished with minimized heat loss through transfer of heat during disinfection from the input fluid in the pre-treatment portion 14 to the output fluid in the post-treatment portion 18. In this way, efficient use of power when disinfecting the apparatus 10 is achieved. Although disinfecting solutions and cleansing solutions may be employed with the present invention, disinfection of an extracorporeal fluid treatment apparatus 10 using the techniques of the present invention may be accomplished without the use of chemical disinfectants such as formaldehyde. Chemical injury to technicians disinfecting an apparatus 10 and container disposal associated with use of chemical disinfects is thereby avoided.

Presently preferred embodiments of the present invention and many of its improvements have been described with a degree of particularity. It should be understood, however, that the present invention is defined by the spirit and scope of the following claims.

What is claimed is:

1. A method for disinfecting an extracorporeal fluid treatment apparatus, said apparatus including an inlet line, an extracorporeal filtration device, a pre-treatment portion operatively connected to the inlet line and to the extracorporeal filtration device, a drain line, and a post-treatment portion operatively connected to the extracorporeal filtration device and to the drain line, said method comprising the steps of:

isolating said pre-treatment portion and said post-treatment portion from said extracorporeal filtration device and from each other;

supplying said pre-treatment portion with an input fluid;

supplying said post-treatment portion with an output fluid;

inducing a flow of said input fluid in said pre-treatment portion;

inducing a flow of said output fluid in said post-treatment portion;

heating said input fluid;

heating said output fluid; and maintaining the flow of heated input fluid in said pre-treatment portion and the flow of heated output fluid in said post-treatment portion until disinfection of both said pre-treatment and post-treatment portions is achieved.

2. The method of claim 1 wherein the step of heating said output fluid further comprises the step of:

heating said output fluid flowing in said post-treatment portion by heat exchange from said input fluid flowing in said pre-treatment portion.

3. A method for disinfecting an extracorporeal fluid treatment apparatus, said apparatus including an inlet line, an extracorporeal filtration device, a pre-treatment portion operatively connected to said inlet line and to said extracorporeal filtration device, a drain line, and a post-treatment portion operatively connected to said extracorporeal filtration device and to the drain line, said method comprising the steps of:

supplying said pre-treatment portion with an input fluid;

inducing a flow of said input fluid in said pre-treatment portion;

creating an input fluid circuit which bypasses said extra-corporeal filtration device and returns said flow of said input fluid in said pre-treatment portion back to said pre-treatment portion;

supplying said post-treatment portion with an output fluid;

inducing a flow of said output fluid in said post-treatment portion;

creating an output fluid circuit which bypasses said extra-corporeal filtration device, isolates said output fluid circuit from said input fluid circuit and returns said flow of said output fluid flowing in said post-treatment portion back to said post-treatment portion;

heating said input fluid flowing in said pre-treatment portion;

heating said output fluid flowing in said post-treatment portion; and maintaining said flow of said heated input fluid flowing in said input fluid circuit and said flow of said heated output fluid flowing in said output fluid circuit until disinfection of both said pre-treatment and post-treatment portions is achieved.

4. The method of claim 3 further comprising the step of:

heating said output fluid flowing in said post-treatment portion by heat exchange from said input fluid flowing in said pre-treatment portion.

* * * * *